US012790941B2

(12) United States Patent
Na et al.

(10) Patent No.: US 12,790,941 B2
(45) Date of Patent: Nov. 10, 2026

(54) INTEGRATED ENVIRONMENTAL MONITORING SYSTEM FOR OIL AND NATURAL GAS WELLS

(71) Applicant: ERG CO., LTD., Seoul (KR)

(72) Inventors: Kyung Won Na, Seoul (KR); Ji Young Lee, Seoul (KR)

( * ) Notice: Subject to any disclaimer, the term of this patent is extended or adjusted under 35 U.S.C. 154(b) by 351 days.

(21) Appl. No.: 18/525,805

(22) Filed: Nov. 30, 2023

(65) Prior Publication Data

US 2025/0084760 A1 Mar. 13, 2025

(51) Int. Cl.

*E21B 47/117* (2012.01)
*E21B 49/08* (2006.01)
*G01N 33/00* (2006.01)

(52) U.S. Cl.

CPC ............ *E21B 47/117* (2020.05); *E21B 49/08* (2013.01); *G01N 33/0075* (2013.01)

(58) Field of Classification Search

CPC .... E21B 47/117; E21B 49/08; G01N 33/0075
See application file for complete search history.

(56) References Cited

U.S. PATENT DOCUMENTS 9,441,430 B2 * 9/2016 Selman .................... E21B 49/08
10,260,316 B2 * 4/2019 Garcia ................ E21B 41/0064
2023/0007082 A1 * 1/2023 Kelly ...................... H04L 67/12

FOREIGN PATENT DOCUMENTS

JP 2015200525 A * 11/2015
KR 101713315 B1 * 3/2017
KR 10-2020-0065400 A 6/2020

* cited by examiner

*Primary Examiner* — Jill E Culler

(57) ABSTRACT

The present invention provides an environmental monitoring system, which includes: a measurement unit configured to measure a gas in an area where operating or abandoned oil and gas wells are installed; a power supply unit configured to supply a power to the measurement unit; and a monitoring unit configured to receive a signal from the measurement unit to monitor gas leakage. According to the present invention as described above, it is capable of integrated environmental monitoring by collecting and measuring gases leaked form the underground and accumulated in an area where operating oil and gas wells or abandoned oil and gas wells are installed, and thereby inducing rapid response as well as appropriate response.

3 Claims, 6 Drawing Sheets

[FIG. 1]
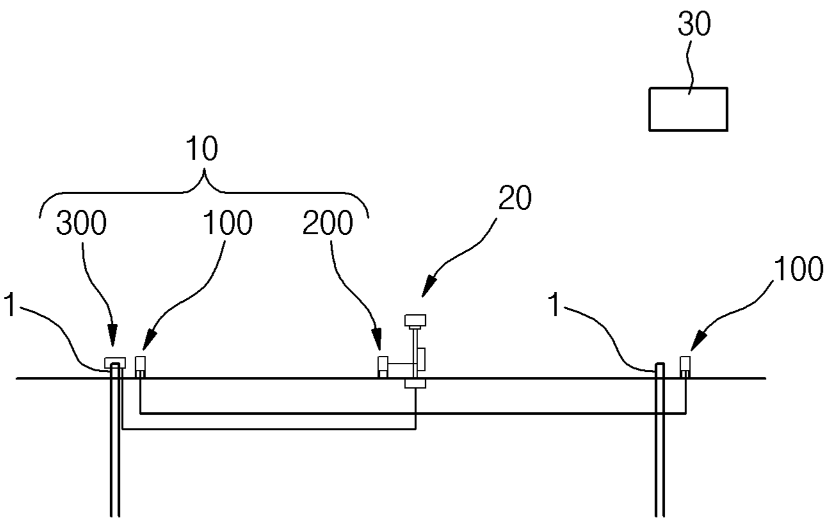
[FIG. 2]
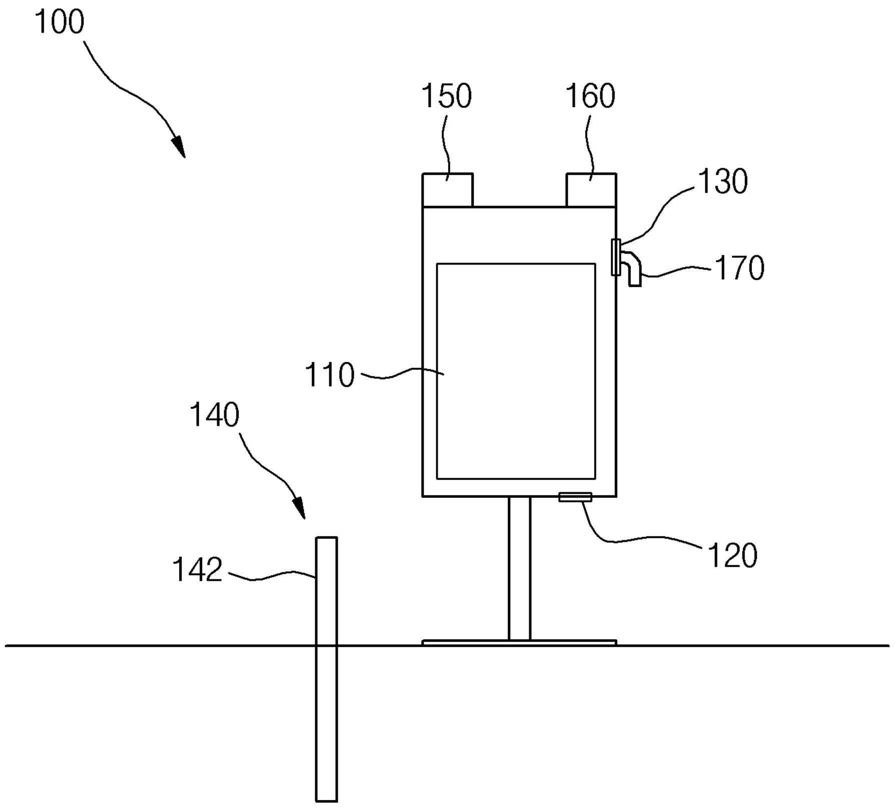

[FIG. 3]
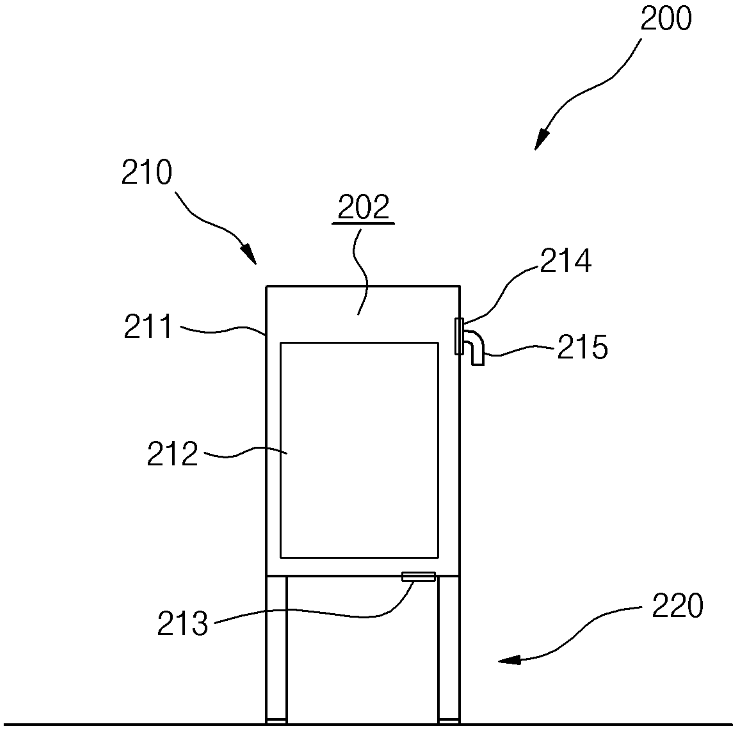

[FIG. 4]
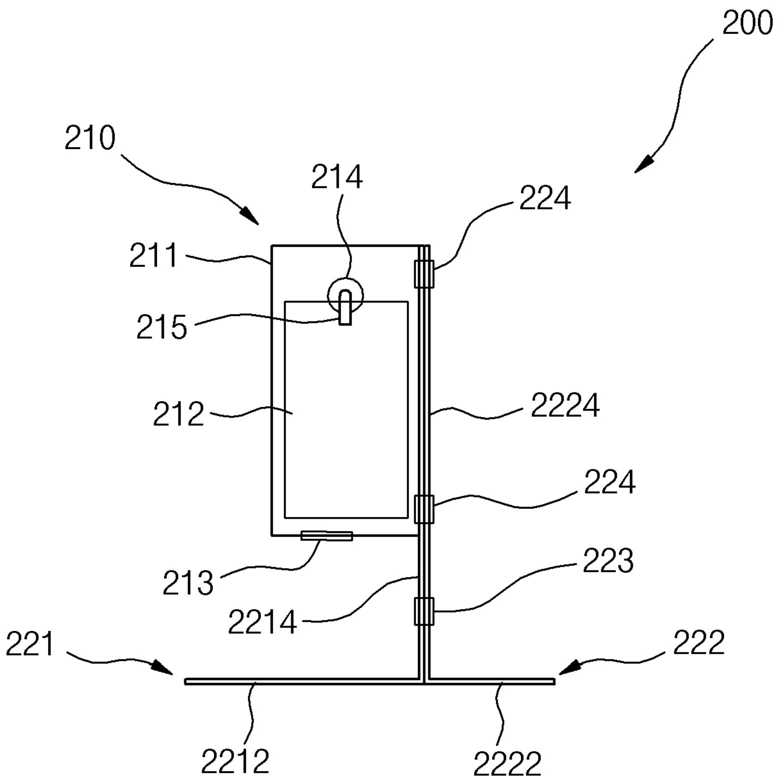
[FIG. 5]
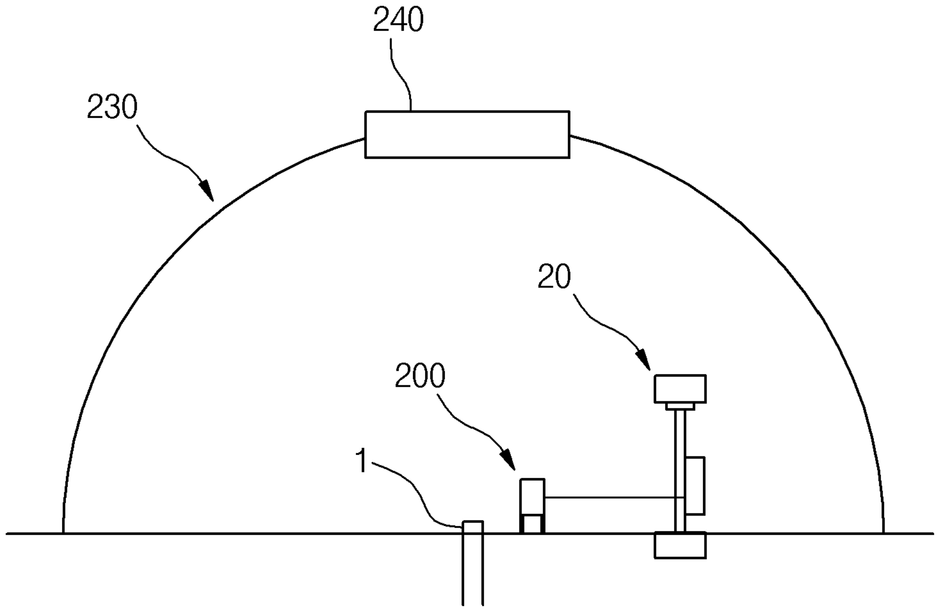

[FIG. 6]
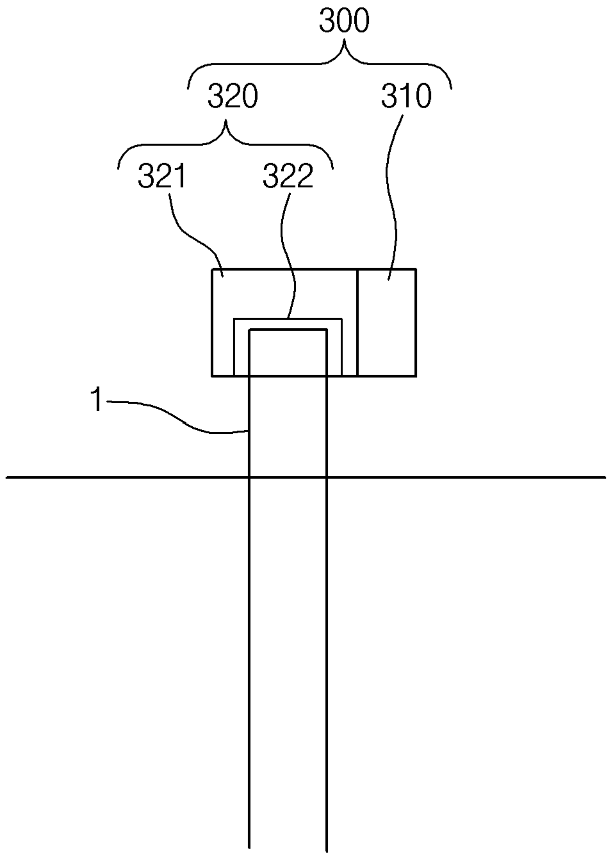

[FIG. 7]
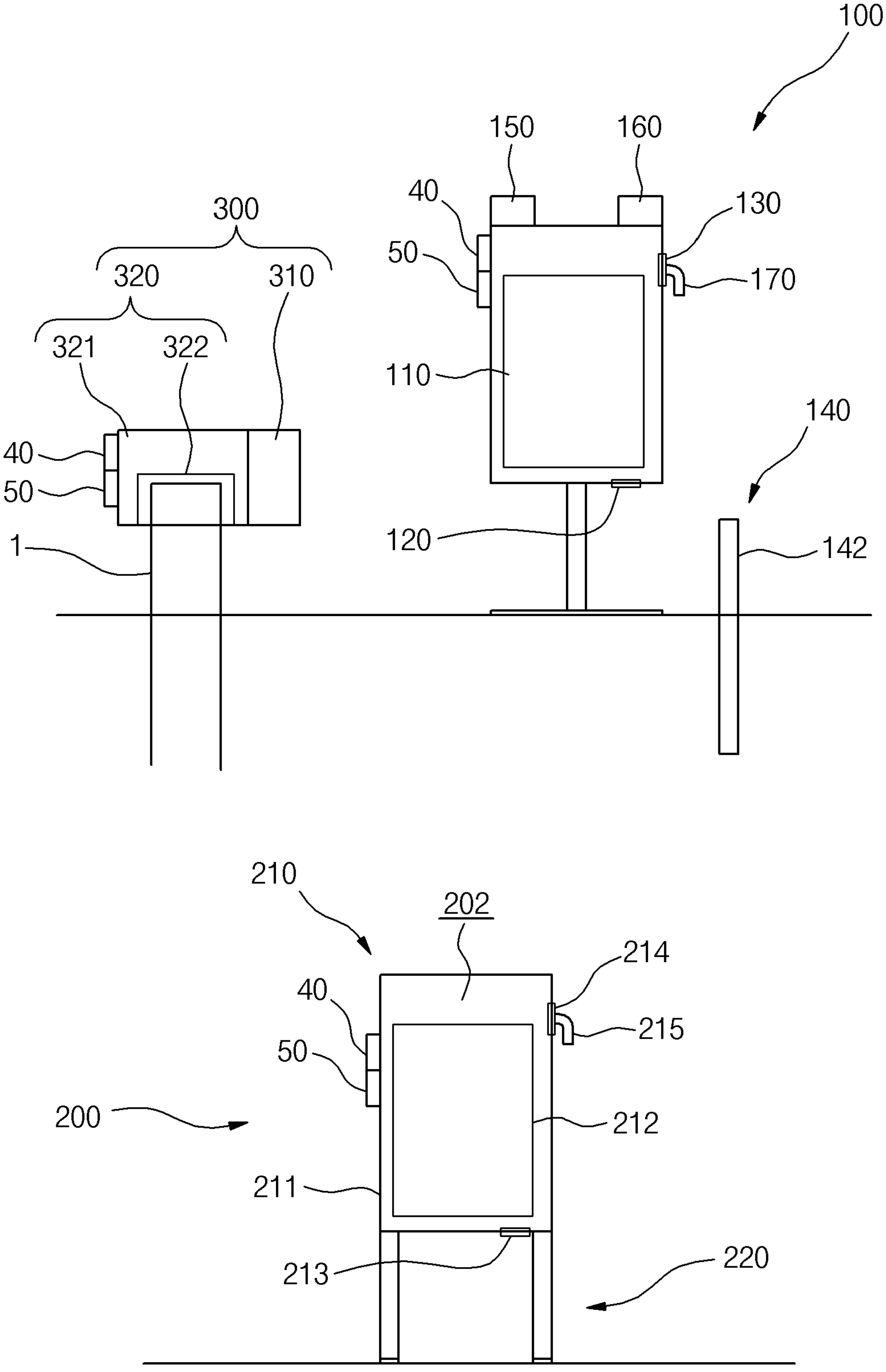

[FIG. 8]
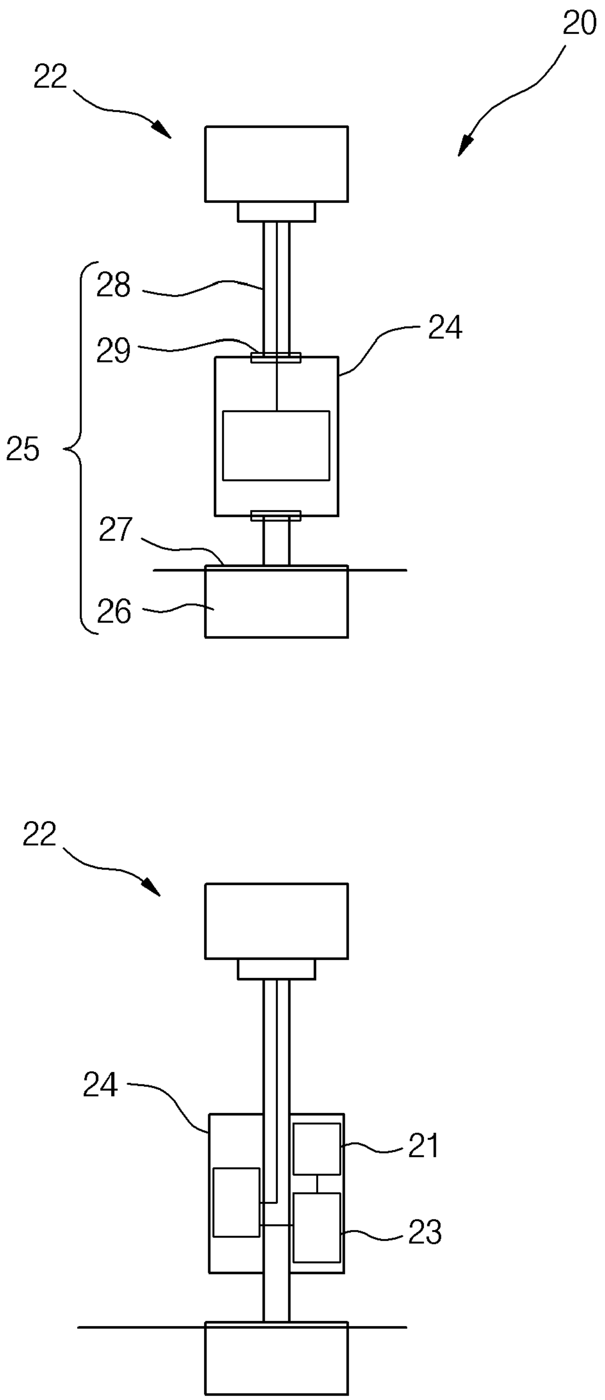

INTEGRATED ENVIRONMENTAL MONITORING SYSTEM FOR OIL AND NATURAL GAS WELLS

CROSS REFERENCE TO RELATED APPLICATIONS

This application claims priority to and the benefit of Korean Patent Application No. 10-2023-0129878 filed on Sep. 11, 2023, the entirety of which is incorporated by reference herein.

Acknowledgement

This work was supported by the Korea Institute of Energy Technology Evaluation and Planning (KETEP) and the Ministry of Trade, Industry & Energy (MOTIE) of the Republic of Korea (No. 20216110100010).

BACKGROUND

Field

The present invention relates to a monitoring system, and more particularly, to an integrated environmental monitoring system for oil and gas (i.e., natural gas) wells, which is capable of integrated environmental monitoring by collecting and measuring gases leaked form the underground and accumulated in an area where operating oil and gas wells or abandoned oil and gas wells are installed, and thereby inducing rapid response as well as appropriate response.

Description of the Related Art

In general, an oil or gas well is subjected to a process of collecting a predetermined amount of oil or gas and then closing it depending on business value. In this case, a pipe installed for collection of the oil or gas is closed to prevent harmful gases from leaking to an outside.

However, despite closing these abandoned wells, problems such as leakage of harmful gases may occur, such that continuous monitoring on the area around the wells is required.

To this end, as disclosed in Korean Patent Application No. 10-2018-0151843 (Laid-open Publication No. 10-2020-00654), a system, which is intended to find a place where gas is leaking, is known in the art. However, since gas leakage occurs not only in the abandoned wells but also in the surrounding underground, a gas may be leaked through the ground, such that accurate monitoring for the gas leakage is impossible.

In order to solve these problems, the development of technique that can monitor the environment around the abandoned wells is urgently required.

SUMMARY

Accordingly, in consideration of the above-described circumstances, it is an object of the present invention to provide an integrated environmental monitoring system for oil and gas wells, which includes: a measurement unit for measuring a gas in an area where operating or abandoned oil and gas wells are installed; a power supply unit for supplying a power to the measurement unit; and a monitoring unit for receiving a signal from the measurement unit to monitor gas leakage, and is capable of integrated environmental monitoring by collecting and measuring gases leaked form the underground and accumulated in an area where operating oil and gas wells or abandoned oil and gas wells are installed, and thereby inducing rapid response as well as appropriate response.

To achieve the above object, according to an aspect of the present invention, there is provided an integrated environmental monitoring system for oil and gas wells, which includes: a measurement unit configured to measure a gas in an area where operating or abandoned oil and gas wells are installed; a power supply unit configured to supply a power to the measurement unit; and a monitoring unit configured to receive a signal from the measurement unit to monitor gas leakage.

Preferably, the measurement unit includes: a real-time measurement unit configured to measure air pollution sources flowing toward the ground adjacent to each operating or abandoned oil and gas well in real time; a cumulative measurement unit configured to measure air pollution sources accumulated over a predetermined period of time in the area where the oil and gas wells are installed; and a temporary measurement unit which is temporarily disposed at a predetermined location in the area before checking problems with the oil and gas wells or before closing them to measure the air pollution sources.

In addition, the real-time measurement unit includes: a real-time measurement sensor installed at a predetermined height to measure air pollution sources which may be generated in the oil and gas wells; a real-time measurement induction part configured to induce air around the oil and gas wells to the real-time measurement sensor; and a real-time measurement discharge part configured to discharge the induced air that has passed through the real-time measurement sensor.

In addition, the real-time measurement sensor measures at least one of volatile organic compounds, methane gas, hydrogen sulfide, carbon monoxide, carbon dioxide, and ozone.

In addition, the real-time measurement unit further includes a real-time underground sensor having a probe inserted into the underground at a predetermined depth around the oil and gas wells, and configured to measure underground pollution sources in real time.

Further, the real-time underground sensor detects total petroleum hydrocarbon materials in soil and water bearing layers.

In addition, the real-time measurement unit further includes: a temperature sensor configured to measure a temperature around the oil and gas wells; and a humidity sensor configured to measure a humidity around the oil and gas wells.

In addition, the cumulative measurement unit includes: a cumulative sensing unit configured to sense a gas in the corresponding area; and cumulative mounting units configured to mount the cumulative sensing unit close to the ground.

Further, the cumulative sensing unit includes: a cumulative measurement case having a sensing space formed therein; a cumulative sensor provided in the sensing space; a cumulative inflow part configured to introduce an outdoor air into the sensing space; and a cumulative discharge part through which the gas in the sensing space is discharged when the outdoor air is introduced therein by the cumulative inflow part.

In addition, the cumulative inflow part is provided at a lower surface of the cumulative measurement case, and the cumulative discharge part is provided at an upper end portion on a side of the cumulative measurement case.

In addition, the real-time measurement unit further includes a circulation guide part configured to guide the gas discharged through the cumulative discharge part toward the cumulative inlet part to facilitate the introduction of outdoor air therein.

In addition, the circulation guide part is a bent pipe whose one end is connected to the cumulative discharge part and the other end is formed to face a lower side where the cumulative inflow part is located, such that the discharged gas circulates the outdoor air around the cumulative inflow part to guide the introduction thereof.

Further, the cumulative measurement case includes: a case body having a sensing space formed therein; and a case door pivotally provided in the case body to open and close the sensing space.

In addition, the accumulation sensor includes at least one of a VOCs sensor, a CH4 sensor, an H25 sensor, an O3 sensor, a CO sensor, and a CO2 sensor.

Further, the cumulative mounting unit includes: a first frame which has a first support frame in contact with the ground and a first installation frame integrally connected to a rear end portion of the first support frame to be erected in contact with a rear surface of the cumulative measurement case; a second frame which is formed in a direction opposite to the first support frame, and has a second support frame in contact with the ground and a second installation frame integrally connected to a front end portion of the second support frame to be erected in contact with the first installation frame; a first mounting fixture configured to fix the first installation frame and the second installation frame to each other; and second mounting fixtures configured to fix the first installation frame and the second installation frame to the cumulative measurement case.

In addition, the cumulative mounting units are fixed to one end portion and the other end portion of the rear surface of the cumulative measurement case, respectively.

In addition, the system further includes: a dome to cover the corresponding area; and a dome ventilation unit provided in the dome to ventilate an interior thereof.

Further, the temporary measurement unit includes: a gas emission unit configured to intentionally emit methane around the oil and gas wells or in a predetermined section of the ground; and a temporary sensor unit configured to detect a gas in the section where the methane has been emitted by the gas emission unit.

Further, the temporary sensor unit includes: a temporary sensor case which forms an external shape thereof, and a temporary fixture configured to mount the temporary sensor case on a section where it is installed in the area.

In addition, the temporary fixture is configured in at least one of a manner to be mounted on the ground and a manner to be hung on a hook.

In addition, the system further includes: GPS sensors configured to measure monitoring positions of the real-time measurement unit, the cumulative measurement unit and the temporary measurement unit; and a data transmission unit configured to transmit signals from the real-time measurement unit, the cumulative measurement unit and the temporary measurement unit to the monitoring unit.

In addition, the power supply unit includes: a regular power supply to which a power is applied from an outside; an eco-friendly power supply configured to generate a power using natural energy; and a rechargeable battery.

Further, the eco-friendly power supply includes at least one of a configuration which produces electricity using solar energy and a configuration which produces electricity using wind energy.

In addition, the rechargeable battery is provided to be replaced and may be charged with at least one of the regular power supply and the eco-friendly power supply.

The rechargeable battery is installed inside an openable power case, and is installed on the ground by a power mounting unit.

In addition, the power mounting unit includes: a base installed in the ground; a base plate installed on the base; a pole installed on the base plate; and a power fixture configured to fix the power case to the pole.

According to the integrated environmental monitoring system for oil and gas wells of the present invention, it is a very useful and effective invention capable of integrated environmental monitoring by collecting and measuring gases leaked form the underground and accumulated in an area where operating oil and gas wells or abandoned oil and gas wells are installed, and thereby inducing rapid response as well as appropriate response.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a schematic view illustrating an integrated environmental monitoring system for oil and gas wells according to the present invention;

FIG. 2 is a schematic view illustrating a real-time measurement unit according to the present invention;

FIG. 3 is a schematic view illustrating a cumulative measurement unit according to the invention;

FIG. 4 is a schematic view illustrating a cumulative mounting unit according to the present invention;

FIG. 5 is a schematic view illustrating a state in which a dome and a dome ventilation unit according to the present invention are further provided;

FIG. 6 is a schematic view illustrating a temporary measurement unit according to the present invention;

FIG. 7 is a schematic view illustrating a GPS sensor and a data transmission unit according to the present invention; and FIG. 8 is a schematic view illustrating a power supply unit according to the present invention.

DETAILED DESCRIPTION OF EMBODIMENTS

Hereinafter, preferred embodiments according to the present invention will be described in detail with reference to the accompanying drawings. The detailed description to be described below with reference to the accompanying drawings is intended to illustrate exemplary embodiments of the invention and is not intended to represent the only embodiment in which the invention may be executed. The following detailed description includes specific details in order to provide a complete understanding of the present invention. However, those skilled in the art will appreciate that the present invention may be executed without these specific details.

In some cases, well-known structures and devices will not be described or will be illustrated in a block diagram form centering on core functions of each structure and apparatus, to avoid obscuring concepts of the present invention.

In the specification, when the explanatory phrase a part "comprises or includes" a component is used, this means that the part may further include the component without excluding other components, so long as special explanation is not given. Further, the term " . . . unit" described in the specification means a unit for processing at least one function or operation. In addition, as used herein the context for describing the present invention (particularly, in the context of the following claims), the singular forms "a," "an," "one" and "the" are intended to include the plural forms as well, unless the context clearly indicates otherwise in the specification or is clearly limited by the context.

In description of preferred embodiments of the present invention, the publicly known functions and configurations that are judged to be able to make the purport of the present invention unnecessarily obscure will not be described in detail. Further, wordings to be described below are defined in consideration of the functions of the present invention, and may differ depending on the intentions of a user or an operator or custom. Accordingly, such wordings should be defined on the basis of the contents of the overall specification.

Hereinafter, preferred embodiments of the present invention will be described with reference to the accompanying drawings.

FIG. 1 is a schematic view illustrating an integrated environmental monitoring system for oil and gas wells according to the present invention, FIG. 2 is a schematic view illustrating a real-time measurement unit according to the present invention, FIG. 3 is a schematic view illustrating a cumulative measurement unit according to the invention, FIG. 4 is a schematic view illustrating a cumulative mounting unit according to the present invention, FIG. 5 is a schematic view illustrating a state in which a dome and a dome ventilation unit according to the present invention are further provided, FIG. 6 is a schematic view illustrating a temporary measurement unit according to the present invention, FIG. 7 is a schematic view illustrating a GPS sensor and a data transmission unit according to the present invention, and FIG. 8 is a schematic view illustrating a power supply unit according to the present invention.

As shown in the drawings, an integrated environmental monitoring system for oil and gas wells includes a measurement unit 10, a power supply unit 20 and a monitoring unit 30.

The measurement unit 10 is provided to measure a gas in an area where operating or abandoned oil and gas wells are installed.

In addition, the power supply unit 20 is provided to supply a power to the measurement unit 10.

The monitoring unit 30 is provided to receive a signal from the measurement unit 10 to monitor gas leakage.

This integrated environmental monitoring system for oil and gas wells monitors whether a harmful gas leaks by collecting, measuring and analyzing gases leaking from oil and gas wells and the underground in the corresponding area.

The corresponding area refers to an area where operating oil and gas wells or abandoned oil and gas wells 1 are located. These abandoned oil and gas wells are sealed to stop using them, but due to the deterioration thereof, leaks to the underground may occur, such that the inventive system is intended to monitor the gas leakage.

To this end, the measurement unit 10 includes a real-time measurement unit 100, a cumulative measurement unit 200 and a temporary measurement unit 300.

The real-time measurement unit 100 measures air pollution sources flowing toward the ground adjacent to each operating or abandoned oil and gas well in real time.

Further, the cumulative measurement unit 200 measures air pollution sources accumulated over a predetermined period of time in the area where the oil and gas wells are installed.

The temporary measurement unit 300 is temporarily disposed at a predetermined location in the area before checking problems with the oil and gas wells or before closing them to measure the air pollution sources.

Here, the real-time measurement unit 100, the cumulative measurement unit 200 and the temporary measurement unit 300 may collect gases from oil and gas wells installed in the same area, thereby enabling comprehensive monitoring of the gases for one area.

Of course, the real-time measurement unit 100, the cumulative measurement unit 200 and the temporary measurement unit 300 may collect and detect gases from oil and gas wells installed in each region, respectively, thereby determining gas leakage for the oil and gas wells installed in the entire region and the corresponding area based on the detected results.

To this end, as shown in FIG. 2, the real-time measurement unit 100 includes a real-time measurement sensor 110, a real-time measurement induction part 120 and a real-time measurement discharge part 130.

The real-time measurement sensor 110 is installed at a predetermined height to measure air pollution sources which may be generated in the oil and gas wells.

Further, the real-time measurement induction part 120 introduces air around the oil and gas wells to the real-time measurement sensor 110.

The real-time measurement discharge part 130 discharges the induced air that has passed through the real-time measurement sensor 110.

Here, the real-time measurement sensor 110 measures at least one of volatile organic compounds, methane gas, hydrogen sulfide, carbon monoxide, carbon dioxide, and ozone, and is installed by including at least one of a volatile organic compounds (VOCs) sensor, a methane (CH4) sensor, an H25 sensor, an ozone (O3) sensor, a carbon dioxide (CO) sensor, and a carbon dioxide (CO2) sensor.

Each of these sensors senses air pollution sources contained in the air flowing through the real-time measurement induction part 120, and the air that has been sensed is discharged into the atmosphere through the real-time measurement discharge part 130.

Accordingly, air pollution sources leaking from each operating or abandoned oil and gas well and air pollution sources flowing toward the ground adjacent to the oil and gas wells are measured in real time.

This real-time measurement unit 100 further includes a real-time underground sensor 140.

This real-time underground sensor 140 has a probe 142 inserted into the underground at a predetermined depth around the oil and gas wells, and is configured to measure underground pollution sources in real time.

This real-time underground sensor 140 detects total petroleum hydrocarbon materials in soil and water bearing layers.

Here, the real-time measurement unit 100 further includes a temperature sensor 150 and a humidity sensor 160.

This temperature sensor 150 measures a temperature around the oil and gas wells, and the humidity sensor 160 measures a humidity around the oil and gas wells.

Accordingly, the inventive system detects and monitors the temperature, humidity and air pollution sources of the oil and gas wells and surrounding regions thereof, as well as total petroleum hydrocarbon materials in the ground in real time.

Further, the real-time measurement unit 100 further includes a real-time circulation guide part 170.

This real-time circulation guide part 170 is provided to guide the gas discharged through the real-time measurement discharge part 130 toward the real-time measurement induction part 120 to facilitate the introduction of outdoor air into the real-time measurement induction part 120.

This real-time circulation guide part 170 is a bent pipe whose one end is connected to the real-time measurement discharge part 130, and the other end is formed to face a lower side where the real-time measurement induction part 120 is located, such that the discharged gas circulates the outdoor air around the real-time measurement induction part 120 to guide the induction thereof.

Of course, this real-time circulation guide part 170 may well be rotatably provided in the real-time measurement discharge part 130, such that the orientation thereof can be adjusted in a direction where the air is discharged as necessary.

Further, as shown in FIG. 3, the cumulative measurement unit 200 includes a cumulative sensing unit 210 and a cumulative mounting units 220.

This cumulative sensing unit 210 is installed to sense gases in the corresponding area. The cumulative mounting unit 220 mounts the cumulative sensing unit 210 close to the ground.

This cumulative measurement unit 200 measures the accumulated air pollution sources by measuring the air in a predetermined size of the area where the oil and gas wells are installed.

To this end, the cumulative sensing unit 210 includes a cumulative measurement case 211, a cumulative sensor 212, a cumulative inflow part 213 and a cumulative discharge part 214.

The cumulative measurement case 211 has a sensing space 202 formed therein.

Further, the accumulation sensor 212 is provided in the sensing space 202.

The cumulative inflow part 213 is provided to introduce an outdoor air into the sensing space 202.

In addition, the gas in the sensing space 202 is discharged through the cumulative discharge part 214 when the outdoor air is introduced therein by the cumulative inflow part 213.

Here, the cumulative inflow part 213 is provided at a lower surface of the cumulative measurement case 211, and the cumulative discharge part 214 is provided at an upper end portion on a side of the cumulative measurement case 211.

In addition, the cumulative sensing unit 210 further includes a circulation guide part 215.

This circulation guide part 215 is provided to guide the gas discharged through the cumulative discharge part 214 toward the cumulative inflow part 213 to facilitate the introduction of outdoor air into the cumulative inflow part 213.

This circulation guide part 215 is a bent pipe whose one end is connected to the cumulative discharge part 214 and the other end is formed to face a lower side where the cumulative inflow part 213 is located, such that the discharged gas circulates the outdoor air around the cumulative inflow part to guide the introduction thereof.

Of course, this circulation guide part 215 may well be rotatably provided in the cumulative discharge part 214, such that the orientation thereof can be adjusted in a direction where the gas is discharged as necessary.

Further, the cumulative measurement case 211 includes a case body and a case door.

The case body has a sensing space 202 formed therein.

In addition, the case door is pivotally provided in the case body to open and close the sensing space 202.

In addition, the cumulative sensor 212 includes at least one of the VOCs sensor, CH4 sensor, H25 sensor, O3 sensor, CO sensor, and CO2 sensor. Of course, sensors suitable for the oil and gas wells in the corresponding area may well be installed.

Further, as shown in FIG. 4, the cumulative mounting unit 220 includes a first frame 221, a second frame 222, a first mounting fixture 223, and second mounting fixtures 224.

The first frame 221 includes a first support frame 2212 in contact with the ground and a first installation frame 2214 integrally connected to a rear end portion of the first support frame 2212 to be erected in contact with a rear surface of the cumulative measurement case 211.

In addition, the second frame 222 is formed in a direction opposite to the first support frame 2212, and includes a second support frame 2222 in contact with the ground and a second installation frame 2224 integrally connected to a front end portion of the second support frame 2222 to be erected in contact with the first installation frame 2214.

The first mounting fixture 223 is provided to fix the first installation frame 2214 and the second installation frame 2224 to each other.

Further, the second mounting fixtures 224 are intended to fix the first installation frame 2214 and the second installation frame 2224 to the cumulative measurement case 211, and the cumulative measurement case 211 is fixed across an upper end portion and a middle potion of the first installation frame 2214 so as to be spaced apart from the first support frame 2212 at a predetermined distance.

The cumulative mounting units 220 are fixed to one end portion and the other end portion of the rear surface of the measurement case 211, respectively.

In addition, as shown in FIG. 5, the integrated environmental monitoring system for oil and gas wells further includes a dome 230 and a dome ventilation unit 240.

The dome 230 is provided to cover the corresponding area, and is configured to cover the corresponding area based on the old oil and gas wells.

In addition, the dome ventilation unit 240 is provided in the dome 230 to ventilate an interior thereof.

Here, the dome 230 is preferably formed at a height that allows a worker to enter and exit, and after the dome ventilation unit 240 is maintained in a closed state for a predetermined period of time, it is checked whether a gas leaks from the corresponding area by measuring the gas by the cumulative measurement unit 200.

Thereafter, the dome ventilation unit 240 is opened to achieve ventilation, and then closed again to repeat the above process.

Further, as shown in FIG. 6, the temporary measurement unit 300 includes a gas emission unit 310 and a temporary sensor unit 320.

The gas emission unit 310 intentionally emits methane (CH4) around the oil and gas wells or in a predetermined section of the ground.

In addition, the temporary sensor unit 320 senses the gas in and around an area where methane (CH4) is leaked by the gas emission unit 310 and transmits it to the monitoring unit 30.

According to this temporary measurement unit 300, it is temporarily installed in an area where leakage of air pollution sources is expected to measure air, and specifically, it is temporarily installed in a location where the real-time measurement unit 100 is not installed.

Of course, the temporary measurement unit 300 may well also be installed in the area where the real-time measurement unit 100 is installed.

To this end, the temporary sensor unit 320 includes a temporary sensor case 321 and a temporary fixture 322.

The temporary sensor case 321 forms an external shape of the temporary sensor unit, and the temporary fixture 322 mounts the temporary sensor case 321 on a section where it is installed in the corresponding area.

This temporary fixture 322 is fixed by at least one of a manner to be erected on the ground and a manner to be hung on a hook.

As shown in FIG. 7, the integrated environmental monitoring system for oil and gas wells includes GPS sensors 40 and a data transmission unit 50.

The GPS sensors 40 are installed to measure monitoring positions of the real-time measurement unit 100, the cumulative measurement unit 200 and the temporary measurement unit 300.

Further, the data transmission unit 50 transmits signals from the real-time measurement unit 100, the cumulative measurement unit 200 and the temporary measurement unit 300 to the monitoring unit 30.

This GPS sensor 40 may check respective location data of the real-time measurement unit 100, the cumulative measurement unit 200 and the temporary measurement unit 300, and the data transmission unit 50 transmits the signals from each GPS sensor 40 to the monitoring unit 30.

Accordingly, the monitoring unit 30 may comprehensively monitor environmental conditions of the oil and gas wells and the corresponding area by using the respective location and detection data of the real-time measurement unit 100, the cumulative measurement unit 200 and the temporary measurement unit 300.

Further, as shown in FIG. 8, the power supply unit 20 includes a regular power supply 21, an eco-friendly power supply 22, and a rechargeable battery 23.

The regular power supply 21 applies a power supplied from an outside to the measurement unit 10, and may also supply the power to the monitoring unit 30.

In addition, the eco-friendly power supply 22 generates electricity using natural energy, and includes at least one of a configuration which produces electricity using solar energy and a configuration which produces electricity using wind energy.

As one embodiment, it is preferable to produce electricity using solar energy, and the configuration which produces electricity using wind power may also be installed together.

In addition, the rechargeable battery 23 is provided to be replaced, and may be charged with at least one of the regular power supply 21 and the eco-friendly power supply 22.

Of course, due to the replaceable manner, the battery may well also be replaced with a new rechargeable battery.

This rechargeable battery 23 is installed inside an openable power case 24, and is installed on the ground by a power mounting unit 25.

This power mounting unit 25 includes a base 26, a base plate 27, a pole 28, and a power fixture 29.

The base 26 is installed in the ground and is buried into the ground.

Further, the base plate 27 is horizontally installed on the base 26 and is fixed thereto with bolts and nuts.

The pole 28 is vertically installed on the base plate 27 and is welded or fixed to the base plate 27 with bolts and nuts.

In addition, the power fixture 29 fixes the power case 24 to the pole 28.

Accordingly, it is possible to safely supply a power to the measurement unit 10.

What is claimed is:

1. An integrated environmental monitoring system for oil and gas wells comprising:

a measurement unit configured to measure a gas in an area where operating or abandoned oil and gas wells are installed;

a power supply unit configured to supply a power to the measurement unit; and a monitoring unit configured to receive a signal from the measurement unit to monitor gas leakage, wherein the measurement unit comprises:

a real-time measurement unit configured to measure air pollution sources flowing toward the ground adjacent to each operating or abandoned oil and gas well in real time;

a cumulative measurement unit configured to measure air pollution sources accumulated over a predetermined period of time in the area where the oil and gas wells are installed; and a temporary measurement unit which is temporarily disposed at a predetermined location in the area before checking problems with the oil and gas wells or before closing them to measure the air pollution sources, wherein the real-time measurement unit comprises:

a real-time measurement sensor installed at a predetermined height to measure air pollution sources generated in the oil and gas wells;

a real-time measurement induction part configured to induce air around the oil and gas wells to the real-time measurement sensor; and a real-time measurement discharge part configured to discharge the induced air that has passed through the real-time measurement sensor;

a real-time underground sensor having a probe inserted into the underground at a predetermined depth around the oil and gas wells, and configured to measure underground pollution sources in real time;

a temperature sensor configured to measure a temperature around the oil and gas wells; and a humidity sensor configured to measure a humidity around the oil and gas wells, wherein the cumulative measurement unit comprises:

a cumulative sensing unit configured to sense a gas in the corresponding area; and cumulative mounting units configured to mount the cumulative sensing unit close to the ground, wherein the cumulative sensing unit comprises:

a cumulative measurement case having a sensing space formed therein;

a cumulative sensor provided in the sensing space;

a cumulative inflow part configured to introduce an outdoor air into the sensing space; and a cumulative discharge part through which the gas in the sensing space is discharged when the outdoor air is introduced therein by the cumulative inflow part, wherein the cumulative inflow part is provided at a lower surface of the cumulative measurement case, and the cumulative discharge part is provided at an upper end portion on a side of the cumulative measurement case, wherein the cumulative sensing unit further comprises a circulation guide part, and the circulation guide part is a bent pipe of which one end is connected to the cumulative discharge part and the other end is formed to face a lower side where the cumulative inflow part is located, such that the discharged gas circulates the outdoor air around the cumulative inflow part to guide the introduction thereof, and wherein the temporary measurement unit comprises:

a gas emission unit configured to intentionally emit methane around the oil and gas wells or in a predetermined section of the ground; and a temporary sensor unit configured to detect a gas in the section where the methane has been emitted by the gas emission unit.

2. The integrated environmental monitoring system for oil and gas wells according to claim 1, further comprising:

GPS sensors configured to measure monitoring positions of the real-time measurement unit, the cumulative measurement unit and the temporary measurement unit; and a data transmission unit configured to transmit signals from the real-time measurement unit, the cumulative measurement unit and the temporary measurement unit to the monitoring unit.

3. The integrated environmental monitoring system for oil and gas wells according to claim 1, wherein the power supply unit comprises:

a regular power supply to which a power is applied from an outside;

an eco-friendly power supply configured to generate a power using natural energy; and a rechargeable battery.

* * * * *